United States Patent [19]

van Hardeveld et al.

[11] 4,109,090

[45] Aug. 22, 1978

[54] A PROCESS FOR PREPARING MELAMINE

[75] Inventors: Rudolf van Hardeveld; Petrus F.A.M. Hendriks, both of Geleen, Netherlands

[73] Assignee: Stamicarbon, B.V., Geleen, Netherlands

[21] Appl. No.: 778,743

[22] Filed: Mar. 17, 1977

[30] Foreign Application Priority Data

Mar. 26, 1976 [NL] Netherlands ........................ 7603164

[51] Int. Cl.[2] ........................................ C07D 251/60

[52] U.S. Cl. ........................................ 544/201; 239/8

[58] Field of Search ........................................ 544/201

[56] References Cited

U.S. PATENT DOCUMENTS 3,377,350 4/1968 Watson et al. ........................ 544/201

*Primary Examiner*—John M. Ford

*Attorney, Agent, or Firm*—Cushman, Darby & Cushman

[57] ABSTRACT

A two phase sprayer and process are disclosed in which the sprayer has a liquid supply tube surrounded by a coaxial gas or gas mixture supply tube which extends beyond the length of the liquid supply tube where the gas flow surrounds and atomizes the expelled liquid. The sprayer has a unique structure in part characterized by a narrowed taper gas supply tube which converges towards the outlet at an angle of 70°-90° with respect to the sprayer axis. The internally-positioned, coaxial liquid supply tube is chamfered also at a similar 70°-90° angle, the gas and liquid tubes at their outlet being essentially parallel.

The joint of the narrowing part of the gas tube and the outflow channel is rounded.

These sprayers efficiently spray relatively large amounts of liquid at low gas velocities and are particularly adapted for spraying a mixture of urea and ammonia into a bed of reactive, fluidized particles to form melamine without destroying desirable features of the fluidized bed into which the urea/ammonia mixture is sprayed.

17 Claims, 2 Drawing Figures

A PROCESS FOR PREPARING MELAMINE

BACKGROUND OF THE INVENTION

This invention relates to a process and device for spraying a liquid by means of an atomizing gas and their application in the preparation of melamine.

It is already known that a liquid can be sprayed by means of a two-phase sprayer consisting of two concentric tubes, in which liquid flows through the central tube and the gas flows through the annular channel between the inner and the outer tube. According to U.S. Pat. No. 3,377,350 the spraying of urea is preferably effected by means of sprayers in which the outflow opening of the gas is in the same plane as the outflow opening of the urea, and the outflow velocity of the gas is preferably higher than the velocity of sound. According to Netherlands Patent Application No. 6,902,755, urea is sprayed by means of sprayers in which the outflow opening of the gas is in front of the outflow opening of the urea, or in which both openings are in the same plane. According to this Patent Application a gas outflow velocity of at most 100 m/sec is used. The sprayers described above all have the drawback that their capacity is limited, because either a poor atomization occurs during spraying, a very large amount of atomizing gas is required, or a high gas velocity is needed in spraying large amounts of liquid, especially molten urea.

The present Application is directed to providing a two-phase sprayer that can also efficiently spray comparatively large amounts of liquid at low gas velocities, preferably at a velocity of at most 100 m/sec.

DETAILED DESCRIPTION OF THE INVENTION

According to the present invention, a suitable two-phase sprayer for liquids, including thin-liquid substances, consists of a tube that is suitable for the supply of liquid which is positioned coaxially in a tube for the supply of atomizing gas so that the gas supply tube extends to a point beyond the outflow opening of the liquid tube, and is characterized in that the gas tube has an inner wall that becomes narrower towards the outlet, is at an angle $\alpha$ to the axis of the sprayer and passes, by way of a rounded wall section, into a comparatively short outflow channel ending at the sprayer outflow opening. As further characterized, the end face of the liquid tube of the outflow opening is chamfered at an angle $\alpha'$ to the axis of the sprayer so that a conical channel with an average apex of between about 140° and about 180° is formed between this wall and the narrowing inner wall of the gas tube. The joint of the narrowing part of the gas tube and the outflow channel is rounded at a radius, which is about 0.1 to about 0.4 times the diameter of the outflow opening of the sprayer. The ratio between the diameter of the outflow opening of the sprayer and the diameter of the outflow opening of the liquid tube ranges between about 1.0 and about 1.6, and the passage area of the sprayer opening is equal to or smaller than the smallest passage area of the conical channel.

The present invention enables sprayers to be built that are capable of spraying large amounts of liquid, for example between 500 and 4500 kg of liquid per hour, using comparatively small amounts of atomizing gas and also at gas outflow rates notably of less than 100 m/sec. We have found that the sprayers according to the present invention exhibit little wear and do not readily become clogged. Moreover, these sprayers are less sensitive to fluctuations in liquid or gas feeds than the well-known sprayers described above.

Liquid sprayers according to the present invention can be used for spraying liquids or thin-liquid substances in general, such as water, aqueous solutions, suspensions or emulsions, organic solvents and compounds that are liquid under normal conditions as well as solutions, suspensions or emulsions in organic solvents, and compounds that have been melted or highly liquefied by heating. Specific examples include water, milk, waste water containing organic compounds in solution, toluene, ethyl acetate, glycerol, petroleum fractions, fuel oil and other liquid fuels, lacquers, molten urea or sulphur, molten polymers and other substances that will be apparent to one skilled in the art.

The sprayers are particularly suitable for spraying substances into a fluidized bed of solid particles. This is so because two advantages are observed: first, proper atomization can be reached at low gas outflow rates so that no or very little wear or pulverization of the solid particles in the bed occurs. Secondly, the sprayers can be designed such that no solid particles are sucked into the sprayer. This strongly reduces the risk of erosion and clogging.

Sprayers according to the present invention constitute a distinct advance in the art, particularly in the fluidized bed field. While there are currently available a number of sprayers that are suitable for spraying liquids such as water, fuel or lacquer into a free space, there is a great need for reliable sprayers that, even at a greater capacity, can spray liquids into a fluid bed with the use of low gas velocities. Sprayers of the present invention are particularly adapted for use in spraying substances into a bed of fluidized particles without untoward effects on the particles.

The sprayers can profitably be used in fluid-bed drying installations and granulators and for injecting fuel or waste water into fluid-bed incinerators. The sprayers are also highly suitable for spraying molten urea into a fluid bed of an inert or catalytically active material by means of ammonia or a mixture of ammonia and carbon dioxide, as is usual in the preparation of melamine based on urea.

Widely diverging gases and mixtures of gases may generally be used as the atomizing gas depending on the nature of the process desired. Examples include hydrogen, air, oxygen, lower hydrocarbons, noble gases, carbon dioxide, nitrogen, ammonia and steam. The choice of the gas depends on the substance to be sprayed and the end use application. The gas may be cooled or preheated as required.

BRIEF DESCRIPTION OF THE DRAWINGS

The present invention is further described with reference to the embodiments shown in the drawing.

Figure 1:
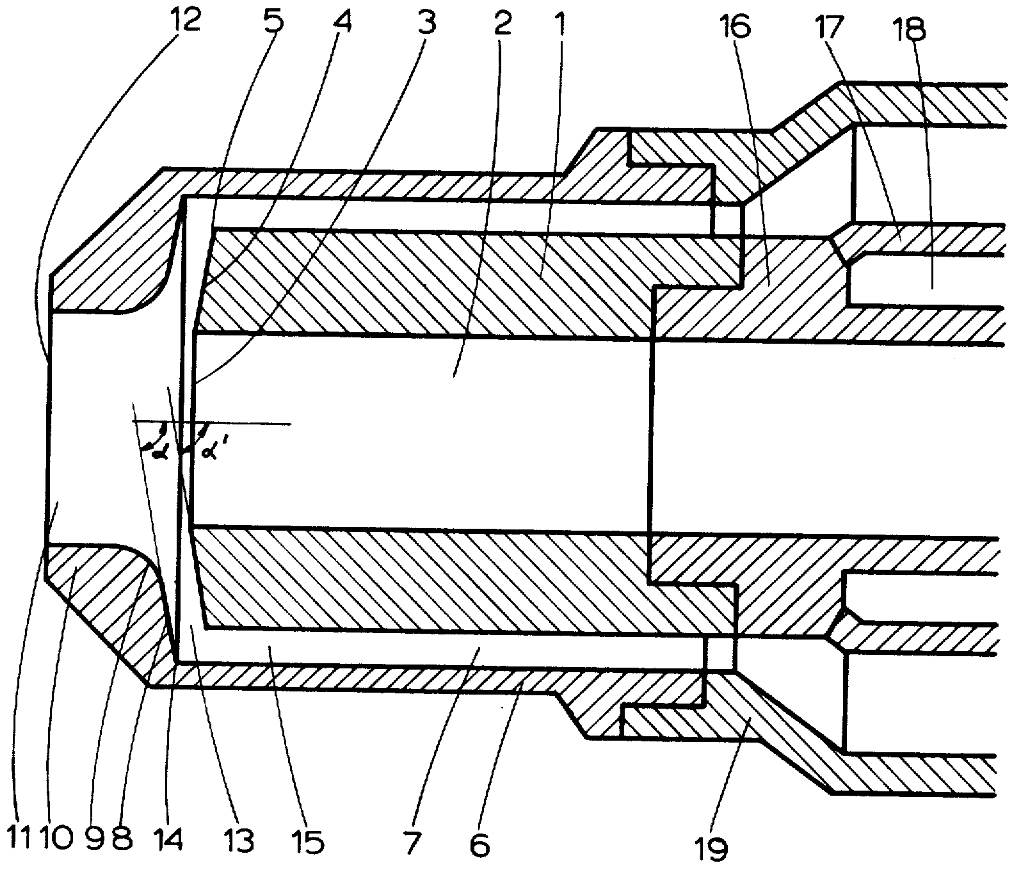
FIG. 1 is a longitudinal section of a sprayer according to the invention.

As the sprayers are radially symmetrical, no cross-section has been shown. The numbers 21–39 in FIG. 2 denote parts which correspond in function with the parts denoted in FIG. 1 by 1–19.

The sprayer body consists of a feed tube 1 for the liquid to be sprayed which tube includes a substantially cylindrical channel 2 for liquid and terminates in an opening 3 that is normal to the direction of flow. End face 4 of tube 1 is chamfered at an angle α' with respect to the axis of the sprayer itself. The edge of the end face and the outer surface are preferably slightly rounded.

A tube 6 is so fitted coaxially around tube 1 defining an annular gas feed channel 7 between the two tubes. Slightly beyond the end of tube 1, tube 6 becomes narrower along the curvature of a wall section 8 that is at an angle α with respect to the sprayer axis, a rounded or shoulder area 9 and a wall section 10, so that a short cylindrical channel 11 is formed which is coaxial and in line with tube 1 and having an outlet opening 12 that is normal to the sprayer axis.

End face 4 of the liquid feed tube and wall section 8 of the gas feed tube enclose a conical channel 13 with an average apex of 140°-180°. Joint 14 of the inner side of tube 6 to wall section 8 may be slightly rounded.

As used herein the expression average apex refers to the average value of the angles 2 × α and 2 × α'. At angles of 70° or less the capacity of the sprayer is limited and at angles of 90° or more the sprayer is susceptible to turbulence in the gas flow thus a specific angle will be selected for use between the two limits of this general range. Preferably the sprayers have the average direction of flow at an angle of between 75° and 87.5° to the axis of the sprayer, and particularly good results are obtained if this angle ranges between 77.5° and 82.5°. Consequently, the average apex is preferably between 150° and 175°, and, more in particular, between 155° and 165°. The size of each of the angles α and α' ranges between 70° and 90°, more preferably between 75° and 87.5° and most preferably between 77.5° and 82.5°.

In determining these angles it is also preferable that α is greater than α' and that the difference between these angles is less than 5°. Special preference is given to the embodiments in which α and α' are completely or virtually substantially equal so that the conical channel thus defined has essentially parallel walls. In combination with the various angles and configurations mentioned above this means that the preferred embodiments of the sprayer according to the present invention exhibit a conical channel having essentially parallel walls with an apex of between 150° and 175° and, more particularly of between 155° and 165°.

Here the angles α and α' and the angle formed by the average direction of flow of the gas and the axis of the sprayer are the same, or virtually the same, and preferably range between 75° and 87.5° and more preferably between 77.5° and 82.5°.

In the embodiments described in detail above comparatively little gas is required for efficient atomization of the liquid while at the same time the chance of turbulence forming in the gas flow and in the outflow opening of the sprayer has been reduced. This is particularly important in sprayers that are used for spraying a liquid into a fluidized bed of solid particles.

Liquid feed tube 1 is connected in a conventional manner, such as by a welded or bolted connection, to liquid feed tube 16, which, in the embodiment shown, is provided with a welded outer jacket 17, so that a space 18 is formed which may be filled with heat-insulating material, adapted to circulate a heat-transfer agent or for an electric heating means.

Tube 16 is connected to a liquid supply source by means of conduits in a conventional manner not shown in the drawing. Tube 6 is connected in a conventional manner to a tube 19 that is connected to a gas supply source in a conventional manner not shown in the drawing.

As will be appreciated from the drawings, the thickness of tube 1 near outflow opening 3 must be such that end face 4 and wall section 8 actually defined a conical channel. In the sprayer embodiment illustrated in FIG. 1, this has been achieved by using a tube with a thick wall so that channel 7 passes, near the end of tube 1, into a channel 15 with the same passage area. In the sprayer embodiment illustrated in FIG. 2, this has been achieved by providing the liquid feed tube with a thicker or enlarged portion near the end of the tube thus with respect to the passage of gas through the tube channel 27 tapers into channel 35 which has a smaller passage area than channel 27.

Outflow channel 11 is comparatively short and in most cases wall section 10 has a length of only between about 1/5 and about ½ the diameter of opening 12. If the outflow channel is longer, there is the risk that the wall 10 will be wetted with liquid. When certain liquids are sprayed, such as molten urea or salt solutions, this might give rise to corrosion. If a comparatively long outflow channel is desired, the channel can be made to flare outwardly. In this case the diameter of the outflow opening of the sprayer is taken to be the smallest diameter in channel 11.

If desired tube 1 may be shaped so that it defines a slightly conical converging or diverging channel 2, but the occurrence of turbulence in the liquid flow must be avoided thus dictating the limits of permissible design changes. However, in all cases, end face 4 is chamfered at an angle α' to the direction of flow as above described.

The ratio between the diameters of the outflow opening 12 of the sprayer and liquid outflow opening 3 ranges between about 1.0 and 1.6 and preferably between about 1.1 and 1.3. These perameters are also controlled by practical use considerations. If the sprayer outflow opening is too small the wall of the outflow channel is wetted by liquid, if the opening is too large the atomization is poor or too large amounts of gas or too high gas velocities are required for proper atomization.

The distance between the end of the urea feed tube and the narrowing inner wall of the gas feed tube, that is the distance between 4 and 8, must be such that the area available for the passage of gas remains the same or becomes smaller towards the outflow opening. Hence, when the gas passes through channel 13 and channel 11 to outflow opening 12 it must have an unchanging or increasing velocity. The velocity preferably increases and hence the passage area in channel 13 is greater than the passage area of the sprayer opening.

The passage area of the conical channel is taken to be the passage area in the part of the channel nearest the sprayer outflow opening. If so desired the gas velocity in the sprayer outflow opening may be lower than the gas velocity in the conical channel, but then the chance of turbulence being formed near the sprayer opening and in the outflow channel, with consequent erosion, increases.

If the sprayer is to be used for spraying liquid into a fluidized bed of catalytically active or inert particles, the end face of the sprayer is preferably rounded or chamfered to reduce wear and to promote suction of the catalyst particles to achieve better mixing of catalyst and liquid.

Rounding of part 9, the shoulder between the narrowing part of the gas feed tube and the outflow channel, is essential for good performance and this too is a matter of careful product design. If the radius of rounding is too small, or if there is no rounding, increased wear is caused by liquid drops or solid particles being drawn onto and into the sprayer head. On the other hand, if the radius of the rounding is too great, too much gas or too high a gas velocity is needed to effect proper atomization. The radius of rounding of part 9 must be chosen so as to prevent or greatly minimize the formation of turbulence in the gas flow. This is achieved by choosing the radius of rounding between about 0.1 and about 0.4 times the diameter of the outflow opening of the sprayer, preferably between about 0.125 and 0.375, and more preferably between 0.2 and 0.3 times this diameter. We have also found that it is preferable to have edge 5 between the outer wall of the liquid feed tube and the end face slightly rounded to prevent turbulence in the gas flow.

If this edge is not rounded turbulence will form causing liquid to settle on the end face of the tube and as a result corrosion may in some cases occur. To prevent turbulence, joint 14 is preferably also slightly rounded. In these two cases the exact radius of rounding is not of any criticality. With due observance of the above ratios, the dimensions of the sprayer are determined by the desired capacity of the sprayer and a capacity of over 4000 kg of liquid/hour can be reached without further adjustments or design changes. The sprayer is constructed of any material that is non-corrosive, dimensionally stable and wear-resistant under the operating conditions. Materials we have found to be suitable include: Inconel, Hastalloy B and Hastalloy C. Other known materials will be known to those skilled in the art depending upon the temperature, pressure and environmental conditions to which the sprayer is to be subjected. Portions of the sprayer that are most subject to wear, such as parts 8, 9, and 10, may be lined with a layer of wear-resistant material or may be formed from inserts of highly resistant material such as silicon carbide, tungsten carbide or alumina.

Another aspect of our invention is the use of the sprayer devices above described in a spraying method or process; thus according to another embodiment of our invention, a liquid is sprayed by means of a gas or a gas mixture in a two-phase sprayer comprising a tube for the liquid to be sprayed having an outflow opening normal to the direction of liquid flow and, around this tube, a coaxial tube for supplying the gas which tube extends beyond the end of the liquid tube, and in which the gas flow surrounds and atomizes the outflowing liquid, characterized in that the liquid is supplied with an outflow velocity of between 10 and 200 cm/sec and the gas is supplied as a non-turbulent or slightly turbulent flow having an unchanging or increasing velocity so that the gas flow, which is passed through a conical channel surrounds and atomizes the outgoing liquid flow while the angle between the directions of the gas flow and the liquid flow is between about 70° and 90°, after which the gas and the liquid leave the sprayer together through a short outflow channel that has a smallest diameter of between 1.0 and 1.6 times the diameter of the liquid outflow opening and is rounded in the area where the inner wall of the gas feed tube passes into the outflow channel. This arrangement provides that no or little turbulence occurs in the outgoing flow because of the radius of rounding ranges between 0.1 and 0.4 times the diameter of the outflow channel, while the amount of gas supplied is such that the weight ratio between the gas and the liquid is between 0.1 and 1.0.

The angle at which the gas flow hits the liquid flow preferably ranges between 75° and 87.5° and particularly between 77.5° and 82.5°.

This process is particularly suitable for spraying a liquid into a fluidized bed of solid particles. In this case, the amount of gas used is preferably such that under operating conditions, the outflow velocity of the gas is between about 20 and 120 m/sec and preferably between about 40 and 100 m/sec in order to prevent pulverization of the particles.

The process of this invention has application in a number of areas including spraying fuel or waste flows into a fluid-bed incinerator or in the hydrogenation or gasification of petroleum. We have found that the process is particularly suitable for spraying molten urea into a fluid bed of inert or catalytically active material, as is usual in the preparation of melamine or cyanuric acid. In this case the atomizing gas used is ammonia or a mixture of ammonia and carbon dioxide. The temperature of the urea is at least 133° C and in most cases between 135° and 150° C. The temperature of the gas is not particularly important and may range between 20° and 400° C.

The velocity with which the liquid leaves the feed tube and meets the atomizing gas may be varied within wide limits, notably between 10 and 200 cm/second and preferably between 50 and 150 cm/second.

The amount of gas used is such that the weight ratio between the gas fed in per unit time and the liquid ranges between 0.1 and 1.0 and preferably between 0.2 and 0.5. Amounts of gas larger than indicated above may be used but are not necessary. The velocity with which the gas leaves the sprayer opening under operating conditions varies within wide limits. Useful velocities ranges between 20 and 120 m/sec, and preferred values include gas velocities of between 40 and 100 m/sec and in particular of between 60 and 90 m/sec. When urea is sprayed into a fluidized bed of particles, a preferred embodiment of the invention, the gas velocity must be lower than 120 m/sec and preferably lower than 100 m/sec so as to avoid pulverization of the particles.

The devices and processes according to the present invention are particularly suitable for use in the preparation of melamine, when, by means of a two-phase sprayer, urea is sprayed into a fluidized bed of catalytically active or inactive material in a reactor in which a pressure of between 1 and 25 atmospheres and a temperature of between 300° and 500° C are maintained and which contains one or more fluidized beds, at least one of which consists of catalytically active material. The synthesis of melamine from urea in this general manner is itself known and well described in the art.

The process aspect of the present invention will be further described with reference to the following examples. As it is not practically possible to actually observe the operation of a sprayer under operating conditions when urea is sprayed with ammonia as the atomizing gas, such as in a melamine reactor, for testing purposes water was sprayed in several experiments in various sprayers with air as the atomizing gas. This arrangement enables visual inspection of various sprayers in operation and gives a general indication of the usefulness of a particular sprayer design in accordance with the above description. Applicants have found that sprayers that operate poorly under water and air conditions, also are not suitable for spraying urea.

EXAMPLE 1

Figure 2:
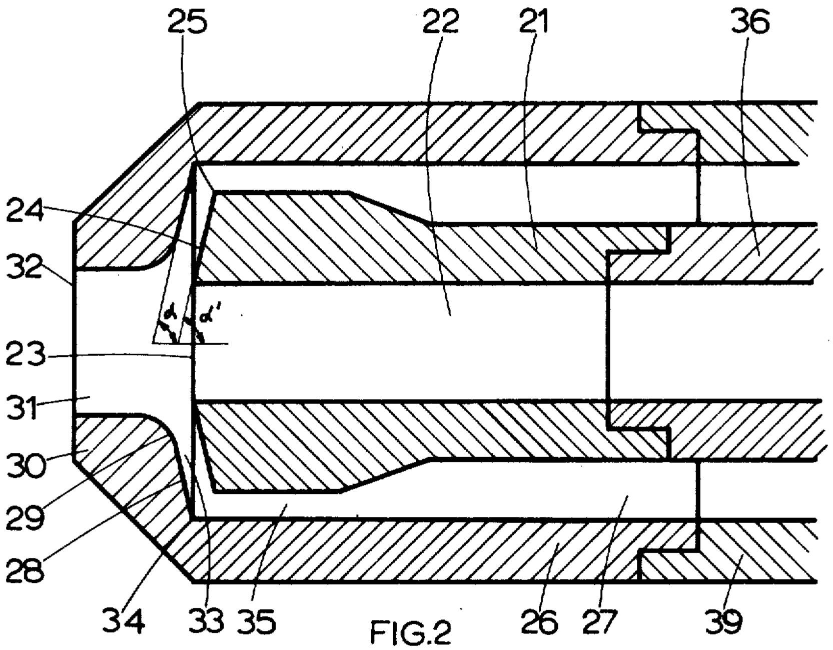
FIG. 2 is a longitudinal section of a modified embodiment of the invention.

Water was sprayed with air as the atomizing gas in a sprayer according to FIG. 1, but in which the transition into the sprayer outflow channel (part 9) was not rounded. The diameter of the sprayer outflow opening was 38 mm, the diameter of the liquid outflow opening was 20 mm and the angles $\alpha$ and $\alpha'$ were 80°. The amount of water sprayed was 2000 kg/hour and the outflow velocity of the air was 116 m/sec. At an equal impelling force of the gas flow per kg of liquid, such an air velocity corresponds to an ammonia velocity of 80 m/sec under operating conditions when urea is sprayed by means of ammonia. The atomization of the water was satisfactory, but an eddy causing inward suction was observed in the outlet of the sprayer. If the same sprayer was used to spray into a fluid bed, this sprayer would suck in particles of fluidized material which would give rise to serious wear from erosion of the sprayer outflow channel.

EXAMPLE 2

Water was sprayed with air as the atomizing gas in a sprayer according to FIG. 1, but again without the rounding of part 9; the diameter of the sprayer outflow opening of the liquid channel was 20 mm and the angles $\alpha$ and $\alpha'$ were 70°. The load was 2000 kg of water per hour and the air outflow velocity was 116 m/sec. The atomization was very poor and an eddy causing inward suction formed in the outflow channel. This did not change at a lower liquid load.

EXAMPLE 3

Water was sprayed with an air outflow velocity of 116 m/sec in a sprayer as described in Example 2, (unrounded part 9), but with a diameter of the outflow opening of the liquid channel of 27 mm. At a load of 1000 kg of water/hour, the atomization was reasonably to good, but at a load of 2000 kg of water/hour, the atomization was poor. In both cases an eddy causing inward suction was observed in the outflow channel.

EXAMPLE 4

2000 kg of water/hour were sprayed with air (outflow velocity of 116 m/sec) in a sprayer according to FIG. 1 with a diameter of the outflow opening of the sprayer of 38 mm, a diameter of the liquid outflow opening of 32 mm, angles $\alpha$ and $\alpha'$ of 80°, a radius of rounding of part 9 of 19 mm, and a length of the outflow channel from the rounded part to the outlet opening of 26 mm. Under these conditions the atomization was not satisfactory, but no turbulence occurred in the outflow channel. Extension of the outflow channel to 40 mm and, in a variant embodiment, to 60 mm, did not improve the atomization. Proper atomization was not reached until at air outflow velocities of over 170 m/sec were reached.

EXAMPLE 5

2000 kg of water/hour were sprayed with air (outflow velocity 116 m/sec) in a sprayer according to FIG. 1 with the following characteristics:

| | |
|---|---|
| diameter of sprayer outflow opening | 38 mm |
| diameter of liquid outflow opening | 32 mm |
| length of outflow channel | 26 mm |

-continued

| | |
|---|---|
| radius of rounding (part 9) | 9 mm |
| radius of rounding (edge 5) | 0.7 mm |
| angles $\alpha$ and $\alpha'$ | 80° |
| distance between walls of conical channel | 6.5 mm |

Under these conditions the sprayer gave excellent atomization without any turbulence near or in the outflow channel. At a liquid load of 3000 kg/h the atomization remained very satisfactory.

EXAMPLE 6

The sprayer described in Example 5 was used for spraying molten urea of about 135° C directly into a fluidized bed of catalytically active material in a melamine reactor with ammonia as the atomizing gas. Under operating conditions the outflow velocity of the ammonia gas was 80 m/sec. while the urea load was varied between 1000 kg of urea/hour and 3600 kg/hour. The reactor and the sprayer were inspected after the sprayer had been operating virtually continuously for 4 months, mostly at a load of about 2000 kg of urea/hour.

The sprayer did not show any signs of erosion. No pronounced signs of corrosion, such as pitting, were observed, either in the reactor itself, or in the heat exchangers fitted in the reactor. From this it may be concluded that the sprayer always operated properly during this period. This is so because if the atomization is poor, drops of urea will hit the reactor wall and the heat exchanger when this type of sprayer is used, so that serious signs of corrosion would soon occur.

What is claimed is:

1. In a process for preparing melamine wherein molten urea is atomized and sprayed into at least one fluidized bed composed at least partly of catalytically active material contained in a reactor, by means of a two-phase sprayer using an atomizing gas selected from the group consisting of ammonia or a mixture of ammonia and carbon dioxide, in which reactor a temperature of between about 300° and 500° C and a pressure of between about 1 and 25 atmospheres are maintained, and wherein said sprayer is comprised of a liquid feed tube adapted for the supply of molten urea, terminating with a liquid outflow opening and positioned around the axis of the sprayer and coaxially within a gas feed tube adapted for the supply of atomizing gas and terminating with a sprayer outflow opening, said liquid and gas feed tubes being adapted such that said gas feed tube extends beyond the liquid outflow opening of said liquid feed tube, the improvement wherein, in said sprayer, said gas feed tube near the sprayer outflow opening has an inner wall section that tapers narrower towards the sprayer outflow opening, at an angle $\alpha$ of between 70° and 90° with respect to the sprayer axis, and continues by way of a rounded shoulder into a comparatively short outflow channel ending at said sprayer outflow opening, said rounded shoulder having a radius of between 0.1 and 0.4 times the smallest diameter of said outflow channel, said liquid feed tube has an outer wall, and an end face between said outer wall and liquid outflow opening chamfered at an angle $\alpha'$ of between 70° and 90° with respect to the sprayer axis thereby forming a conical channel with an average apex of between 140° and 180° between said chamfered end face and the tapered inner wall section of the gas feed tube, and further wherein the passage area of the conical channel at the end adjacent to said outflow channel is no greater than such passage area at any other place within said conical channel, the smallest passage area of said outflow channel is no greater than the smallest passage area of said conical channel, and the smallest diameter of the outflow channel is between 1.0 and 1.6 times the diameter of the liquid outflow opening.

2. The process according to claim 1 wherein the difference in size between the angles $\alpha$ and $\alpha'$ is at most 5°.

3. The process according to claim 2 wherein the angles $\alpha$ and $\alpha'$ are substantially or completely equal and the conical channel thus defined has substantially parallel walls.

4. The process according to claim 1 wherein each of the angles $\alpha$ and $\alpha'$ has a size of between 75° and 87.5°.

5. The process according to claim 4 wherein each of the angles $\alpha$ and $\alpha'$ has a size of between 77.5° and 82.5°.

6. The process according to claim 1 wherein the smallest diameter of the outflow channel is between 1.1 and 1.3 times the diameter of the liquid outflow opening.

7. The process according to claim 1 wherein the radius of said rounded shoulder is 0.2 to 0.3 times the smallest diameter of the outflow channel.

8. The process according to claim 1 wherein the edge formed by the chamfered end face of the urea supply tube and the outer wall of said tube is rounded having a radius that suppresses or prevents the formation of turbulence in the gas flow.

9. The process according to claim 1 wherein the smallest passage area of the outflow channel is smaller than the smallest passage area of the conical channel.

10. The process of claim 1 wherein said molten urea is fed to the sprayer at a rate so as to pass through said liquid outflow opening at a velocity of between 10 and 200 centimeters per second, said atomizing gas is fed to the sprayer at a rate such that the gas flow passing through said conical channel is at most slightly turbulent, and the weight ratio of atomizing gas to molten urea fed to said sprayer is between 0.1 and 1.0, and wherein said atomizing gas leaving said conical channel surrounds and impinges upon said molten urea passing through said liquid outflow opening at an angle between the direction of gas flow and the direction of liquid flow of between 70° and 90° whereby said molten urea is atomized and the resulting gas-liquid mixtures is passed into said melamine reactor via the outflow channel.

11. The process according to claim 10 wherein the atomizing gas flow impinges upon the molten urea flow at an angle of between 75° and 87.5°.

12. The process according to claim 11 wherein the atomizing gas flow impinges upon the molten urea flow at an angle of between 77.5° and 82.5°.

13. The process according to claim 10 wherein the smallest diameter of the outflow channel is between 1.1 and 1.3 times the diameter of the liquid outflow opening.

14. The process according to claim 10 wherein the turbulence in the outflowing gas-liquid mixture is reduced by passing said gas-liquid mixture over said rounded shoulder having a radius of 0.2 to 0.3 times the smallest diameter of the outflow channel.

15. The process according to claim 10 wherein the turbulence in the gas flowing through the conical channel is reduced by passing said gas over a rounding at the edge formed by the outer wall of the liquid supply tube and the chamfered end face of this tube.

16. The process according to claim 10 wherein the atomized molten urea is sprayed directly into a fluidized bed of solid particles with a gas outflow velocity through the sprayer outflow opening of between 20 meters per second and 120 meters per second.

17. The process according to claim 16 wherein the gas outflow velocity ranges between 40 meters per second and 100 meters per second.

* * * * *